United States Patent
Warren et al.

(10) Patent No.: US 6,564,100 B2
(45) Date of Patent: May 13, 2003

(54) CARDIAC RHYTHM MANAGEMENT SYSTEM WITH REMOTELY ACTIVATED CAPTURE VERIFICATION FOR CHF AND OTHER PATIENTS

(75) Inventors: Jay A. Warren, North Oaks, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 238 days.

(21) Appl. No.: 09/731,124

(22) Filed: Dec. 6, 2000

(65) Prior Publication Data

US 2002/0068959 A1 Jun. 6, 2002

(51) Int. Cl.⁷ ................................................. A61N 1/37
(52) U.S. Cl. ...................................................... 607/28
(58) Field of Search ...................... 607/28, 27

(56) References Cited

U.S. PATENT DOCUMENTS 5,843,137 A   12/1998   Condie et al. ................ 607/28

*Primary Examiner*—J. Casimer Jacyna
(74) *Attorney, Agent, or Firm*—Nikolai & Mersereau; Thomas J. Nikolai

(57) ABSTRACT

A cardiac rhythm management device capable of delivering multiple uni-chamber stimulation pulses to a patient's heart and suitable for verifying capture independently for each uni-chamber stimulation pulse. The uni-chamber capture verification mode of the cardiac rhythm management device may be activated via telemetry or by applying a magnetic field proximate the device. During the capture verification mode, bi-chamber pacing, for example, may precede or follow uni-chamber pacing to allow for pacing support. Also, the energy levels of the pacing stimulus over several beats may be varied, thereby verifying the programmed safety margins.

22 Claims, 4 Drawing Sheets

CARDIAC RHYTHM MANAGEMENT SYSTEM WITH REMOTELY ACTIVATED CAPTURE VERIFICATION FOR CHF AND OTHER PATIENTS

FIELD OF THE INVENTION

This invention relates generally to a cardiac rhythm management device capable of determining whether a stimulus delivered to a patient's heart evokes a response. More particularly, this invention relates to a method and device for delivering stimulation pulses to pre-determined chambers within an electrically continuous area of the patient's heart and then determining independently for each stimulation pulse whether the stimulus evokes a response or is "captured" by the corresponding cardiac muscle. The independent determination of capture for each chamber of the patient's heart may be activated via telemetry or by applying a magnetic field proximate the device. The capture verification may be performed manually by a physician utilizing telemetry or may be performed automatically by the device. During the capture verification mode of the present invention, bi-chamber stimulation may precede or follow uni-chamber stimulation to allow for stimulation support during the capture verification mode.

BACKGROUND OF THE INVENTION

Cardiac stimulators typically include a pulse generator, limited power supply, electrical leads coupled thereto, and a controller. The controller typically includes a microprocessor having preprogrammed code, and may include ROM memory for storing programs to be executed by the controller and RAM memory for storing operands used in carrying out the computations by the controller. In order to maximize use of the limited power supply, it is desirable to set the pulse generator's stimulation output at the lowest output energy that reliably causes depolarization of the corresponding cardiac muscle.

To ensure the reliability of "capturing" a stimulation such as a pacing pulse, it is common practice to determine the minimum output energy that induces a cardiac depolarization ("the energy threshold") manually during patient follow-ups, and then set the pacing pulse output at this minimum setting plus a wide error margin, oftentimes double or triple the minimum effective energy. This error margin is meant to account for the changes in energy requirements that may occur over time between patient follow-ups. Typically, when determining the energy threshold of the ventricles, both ventricles are simultaneously stimulated and if depolarization is detected, capture of both ventricles is assumed. It is expected to be far more efficient and/or economic for a pacemaker to determine a threshold for each chamber independently and adjust the output energy settings independently thereby incorporating a much smaller error margin.

For example, oftentimes a cardiac rhythm management device utilized for treating congestive heart failure delivers stimulation therapy to both sides of the heart for either atrial stimulation or ventricular stimulation. The sensing for depolarization signals from the corresponding chambers is non-discriminatory, such that if a depolarization signal is sensed, the device assumes capture in both chambers. The false assumption that the capture threshold is the same in both chambers may reduce the effectiveness of the stimulation therapy. Hence, there is a need for a device that verifies capture independently for stimulation pulses delivered to pre-determined chambers within an electrically continuous area of the patient's heart. The present invention meets these and other needs that will become apparent from a review of the description of the present invention.

SUMMARY OF THE INVENTION

The present invention provides a method and apparatus that may be used, for example, to treat congestive heart failure in a patient. The method and device of the present invention provides for the physician a mechanism for determining whether a stimulation to each pre-selected chamber evokes a response. The cardiac rhythm management device of the present invention generally includes a pulse generator, power supply, controller, leads coupled thereto, and a linkage of known suitable construction to provide for telemetry between the device and an external programmer. The cardiac rhythm management device of the present invention may include a stimulation means for transmitting at least first and second stimulation pulses during a cardiac cycle to an electrically continuous area of the heart, a sensing means for sensing a response to each stimulation pulse, and a controller connected to the stimulation means and sensing means, wherein the controller includes a mode for determining whether each stimulation results in capture.

The mode for determining whether each stimulation output results in capture may be activated by an externally applied magnetic field or may be activated by the physician/programmer via telemetry. The cardiac rhythm management device of the present invention provides uni-chamber stimulation and allows verification of capture for each uni-chamber stimulation. In one embodiment of the present invention, a first stimulation is directed to a right ventricle of the patient and a second stimulation is directed to a left ventricle of the patient. Capture is then determined separately for the left and right ventricle. In another embodiment of the present invention, the first stimulation is directed to the right atrium of the patient and the second stimulation is directed to the left atrium of the patient. Capture is then determined independently for the left and right atrium. In still another embodiment of the present invention, the first stimulation may be directed to a first pre-selected chamber at a first pre-selected site of the patient's heart and the second stimulation may be directed to the same pre-selected chamber at a second pre-selected site of the patient's heart. Those skilled in the art will appreciate that other stimulation sequences may be applied to the atriums or ventricles and then capture may be determined independently in accordance with the present invention.

When the capture verification mode is activated, several first stimulation pulses may be transmitted to the heart prior to transmitting the second stimulation pulses. Those skilled in the art will appreciate that "normal" stimulation pulses or stimulation pulses known to evoke a response may be applied between transmitting the first stimulation pulses and the second stimulation pulses. Application of normal stimulation pulses between the first and second stimulation pulses in affect neutralize any affects the first stimulation may have on the effectiveness of the second stimulation pulses. Further, application of the normal stimulation pulses between the first and second stimulation pulses may provide the patient with pacing therapy if the test pulses did not capture the heart. Also, the stimulation energy of the stimulation pulses may be varied by a predetermined amount to further identify the minimum required energy required to evoke a response by the heart.

In use, the preferred method for verifying capture of stimulation pulses delivered to pre-selected chambers of a patient's heart includes the following steps: activating an algorithm or predetermined parameters of the cardiac rhythm management device via a magnetic field of prescribed strength and duration or other external device; delivering during a cardiac cycle first and second stimulation pulses to an electrically continuous area of the heart in accordance with the algorithm or preset parameters; sensing and monitoring the depolarization waveforms corresponding to each stimulation pulse; and determining whether each stimulation results in capture. The preferred method utilizes a means for sensing cardiac electrogram signals, a programmable controller coupled to receive signals from an external programmer, a telemetry link, an external depolarization monitor and stimulation means for applying cardiac stimulation pulses to a patient's heart in accordance with the timing and energy output determined by the physician or user. The controller may include means for controlling both the pulse generator and the stimulation output generated by the pulse generator, means for determining intrinsic heart cycle lengths, and means for analyzing signals sensed by one or more electrodes after a pre-selected time expires after transmitting a stimulation pulse to another electrode.

Hence, the cardiac rhythm management device of the present invention is capable of allowing independent verification of capture for each ventricle or atrium of the heart. The cardiac rhythm management device includes a capture verification mode that may be activated by applying a magnetic field proximate the device, wherein the capture verification may be controlled via telemetry. Also, the cardiac rhythm management device is capable of delivering stimulation pulses to pre-determined chambers within an electrically continuous area of the patient's heart and thereafter allows independent verification of capture for each stimulation. Also, the cardiac rhythm management device is capable of transmitting "normal" stimulation pulses at pre-determined intervals during the capture verification mode. These and other advantages of the present invention will become readily apparent to those skilled in the art from a review of the following detailed description of the preferred embodiment especially when considered in conjunction with the claims and accompanying drawings in which like numerals in the several views refer to corresponding parts.

DESCRIPTION OF THE PREFERRED EMBODIMENT

Figure 1:
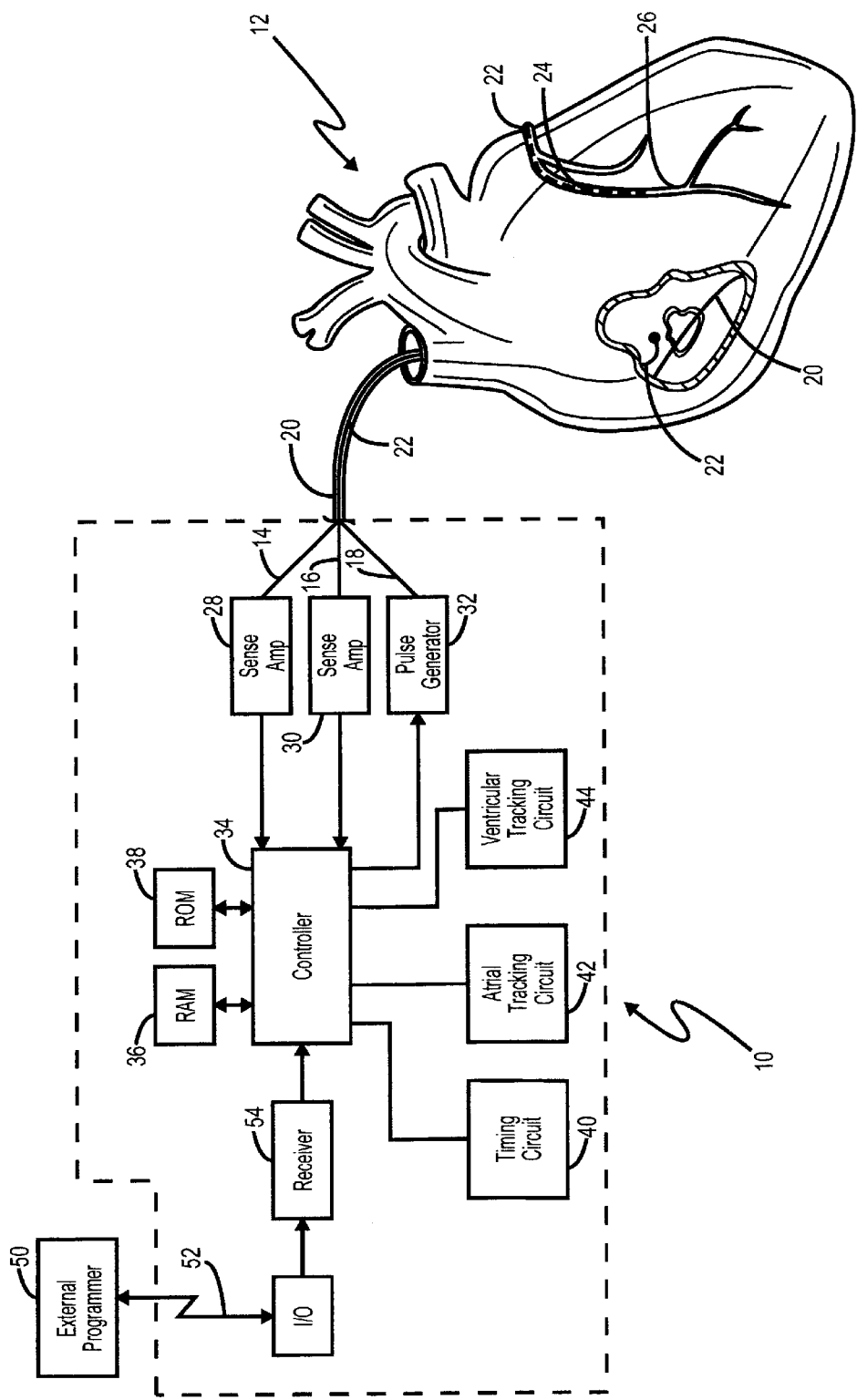
FIG. 1 is a block diagram showing generally the components of the cardiac rhythm management device of the present invention.
Figure 4:
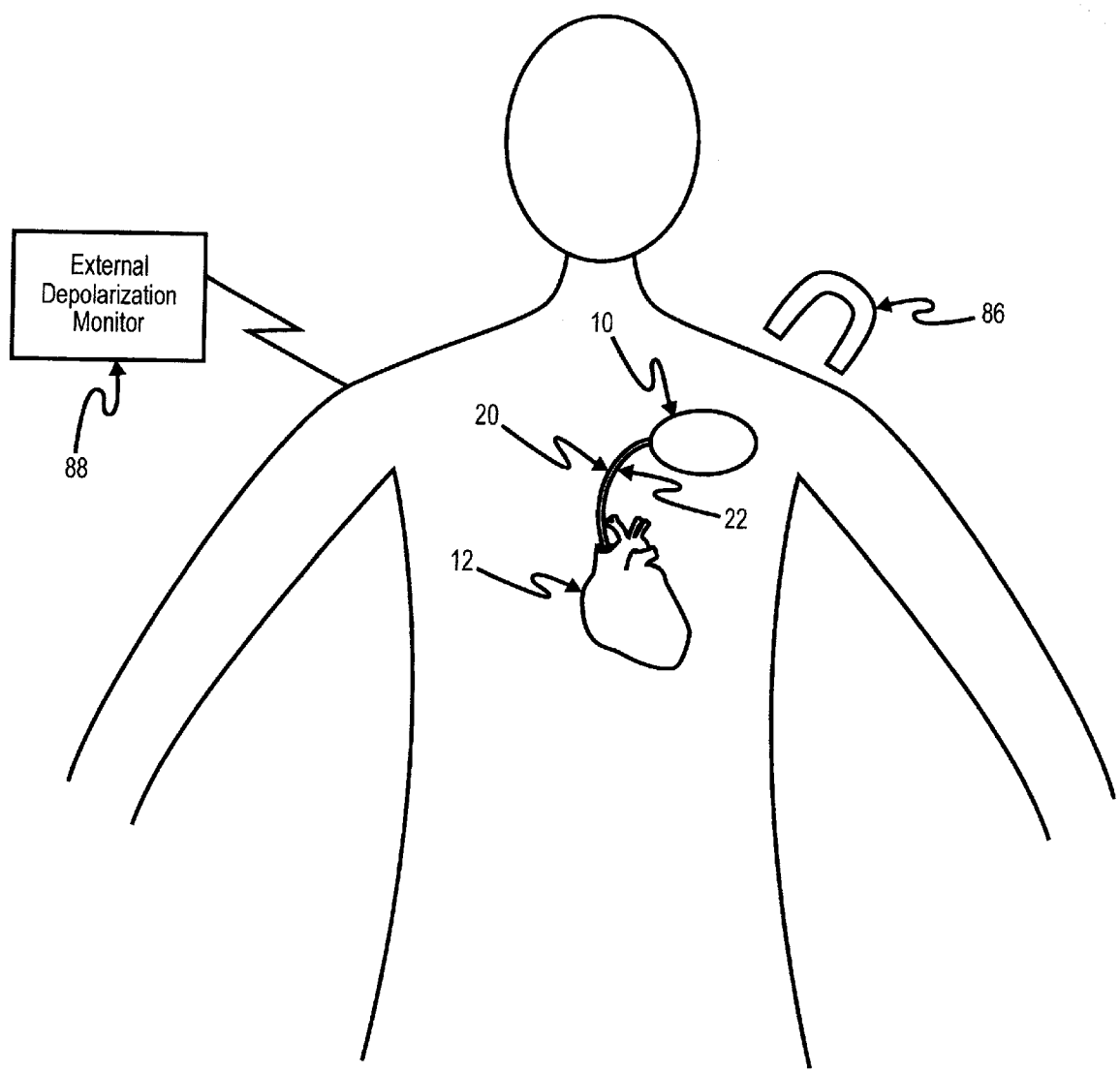
FIG. 4 is illustrates the activation of autocapture via a magnetic field and control of the autocapture sequence via an external depolarization monitor.

The present invention represents broadly applicable improvements to capture verification in cardiac rhythm management devices. The embodiments detailed herein are intended to be taken as representative or exemplary of those in which the improvements of the invention may be incorporated and are not intended to be limiting. Referring first to FIG. 1, there is shown generally in block diagram a cardiac rhythm management device 10 (enclosed by a dotted line) operatively connected to a patient's heart 12 by electrical conductors 14, 16 and 18 which are electrically coupled to stimulation leads 20 and 22. Without limitation, lead 20 may be utilized for stimulating and sensing in the right ventricle and lead 22 may be utilized for stimulating and sensing in the left ventricle. Those skilled in the art will appreciate that other leads and configurations for stimulating pre-selected chambers of the heart, of known suitable construction, may be utilized in conjunction with the method of stimulation and capture detection of the present invention. Lead 22 includes electrodes 24 and 26 positioned proximate the left ventricle. Leads 20 and 22 are electrically coupled to sense amplifiers 28 and 30 respectively and to pulse generator 32. The resulting sensed ventricular events are transmitted to an input of a controller 34. Alternatively, as shown in FIG. 4, an external depolarization monitor 88 may be utilized to determine or "sense" depolarization waveforms associated with a pacing stimulus.

The controller 34 may be programmed to operate in any one of a plurality of stimulation modes. For ease of discussion, and without limitation, a stimulation mode during capture verification will be described in relation to pacing the left and right ventricles. Those skilled in the art will appreciate that the pacing and capture verification mode may be adapted for use in other various stimulation configurations. Also, the physician during capture verification may utilize the external depolarization monitor 88 or alternatively may use a timing circuit 40, atrial tracking circuit 42, and ventricular tracking circuit 44 coupled to the controller. The controller 34 has both RAM (Random Access Memory) 36 and ROM (Read Only Memory) 38 for storing programs and data which allows: the processing of sensed signals, triggering the pulse generator 32, determining a sinus rate from the sensed signal, analyzing the sensed signals, and storing various information derived from this analysis.

During normal pacing, the controller 34 manipulates the pacing therapy, for example, delivered by the pulse generator 32 to one or both of the stimulating leads 20 and 22 (depending upon the stimulation mode selected). An external programmer 50 having a micro-processor and associated memory may transmit information in a conventional way through a telemetry link 52 and transmission receiver 54 of the cardiac rhythm management device 10. Utilizing the programmer 50 and the telemetry link 52, the operating parameter values for the cardiac rhythm management device 10 can be delivered to it by a cardiologist. The cardiologist may set the cardiac cycle-pacing parameter values to be utilized, including various timing intervals. Cardiac stimulating devices capable of telemetry of various status information including selecting the pacing parameters and mode (determined by the physician) are commercially available from, for example, Cardiac Pacemakers, Inc., St. Paul, Minn.

Figure 2:
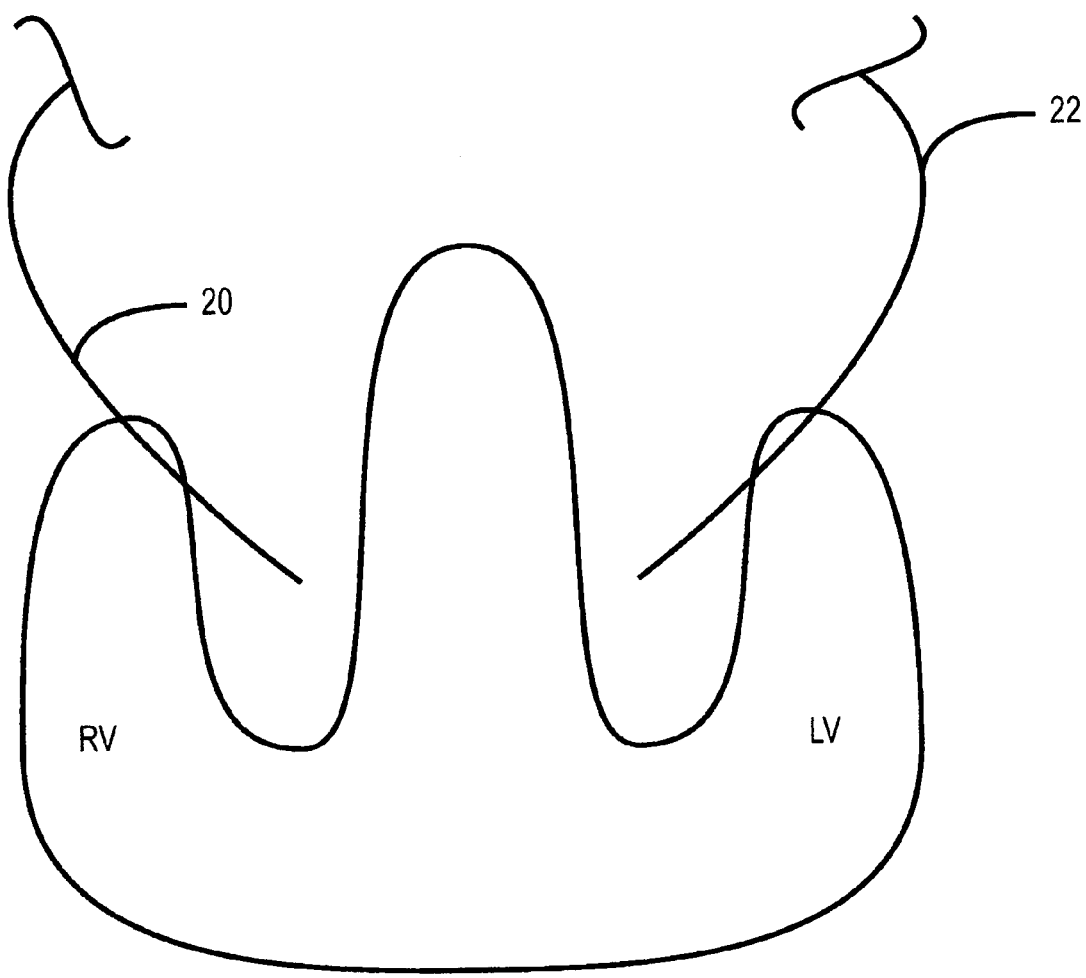
FIG. 2 is a partial sectional view of the ventricular portion of a patient's heart.

Referring next to FIG. 2, a partial sectional view of the ventricular portion (electrically continuous area) of the patient's heart is shown. During the capture verification mode, the cardiac rhythm management device 10 may be programmed to sequentially stimulate both the right and left ventricles through leads 20 and 22 as described in greater detail below.

Figure 3:
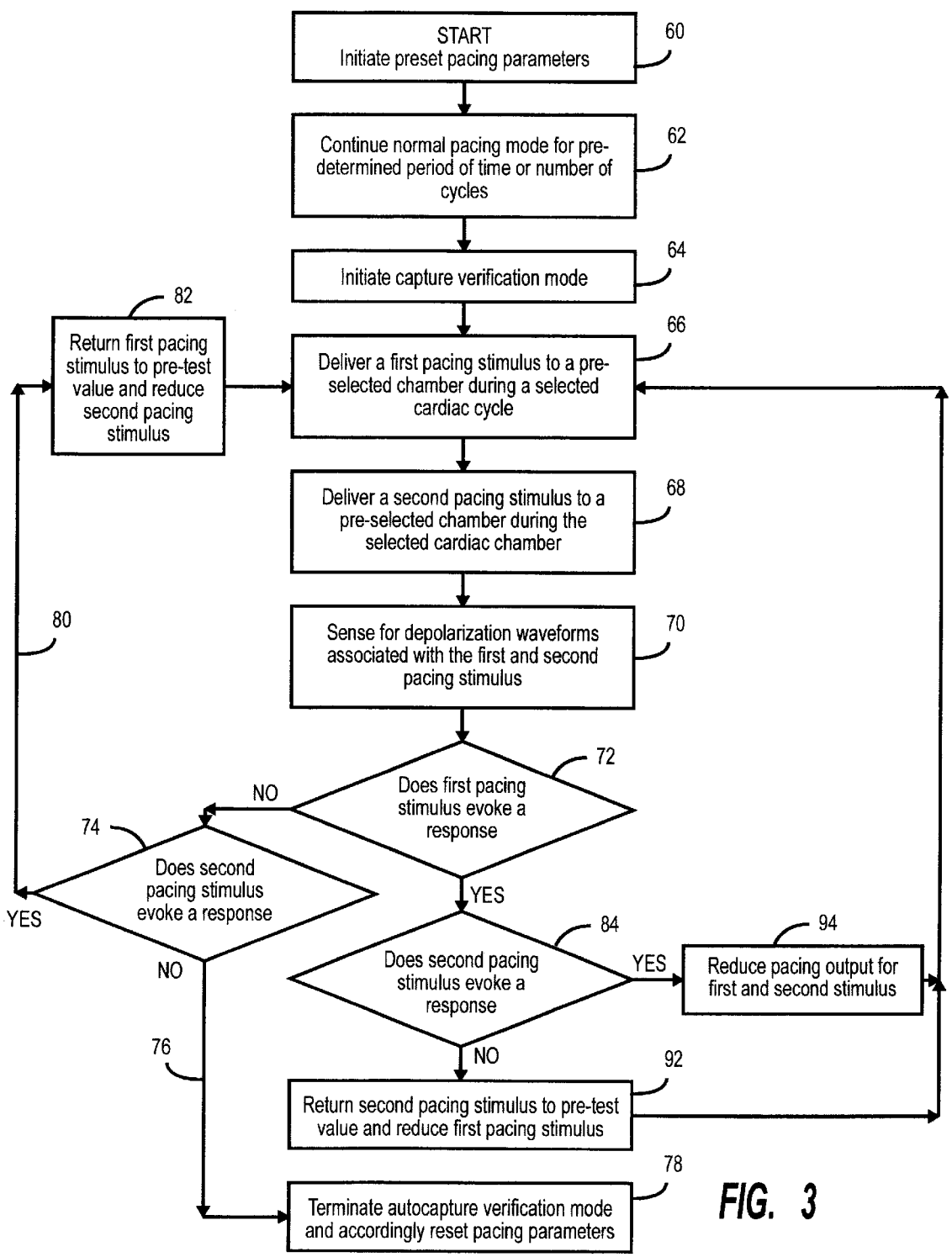
FIG. 3 is a flowchart showing an algorithm that may be used manually or automatically by the cardiac rhythm management device to determine capture independently for each chamber of the patient's heart.

Referring next to FIG. 3, the method of capture verification will next be discussed in greater detail. Those skilled in the art will appreciate that although the method of capture verification of the present invention is implemented by a physician, a cardiac rhythm management device may be programmed to automatically implement the capture verification method of the present invention. The algorithm illustrated in FIG. 3 may be activated and carried out by the physician or alternatively may be activated and carried out by the device. Without limitation, the capture verification mode of the present invention is described relative to pacing the left and right ventricles of a patient's heart, however, those skilled in the art will appreciate that the method described herein may equally apply to other stimulation sequences. The user first initiates preset pacing parameters of the cardiac rhythm management device 10 (see Block 60) and pacing in accordance with the preset "normal pacing mode" continues for a pre-determined period of time or a pre-determined number of cycles (see Block 62). The capture verification mode may be activated (see Block 64) and monitored utilizing an external programmer 50 or autonomously by the device (as shown in FIG. 1). However, in the preferred embodiment, the capture verification mode is initiated by applying a magnetic field proximate the device 10. A magnet or external electronic actuator 86 contained within a hand held unit of suitable known construction, may be utilized to apply the magnetic field proximate the device 10. The magnetic field affects closure of a reed switch, Hall affect device, or other switch of suitable known construction in the implanted device to thereby initiate the capture verification mode.

Once the capture verification mode is initiated, a first pacing stimulus is delivered to a pre-selected chamber during a selected cardiac cycle (see Block 66). A second pacing stimulus is transmitted to a pre-selected chamber during the same selected cardiac cycle (see Block 68). Sense amplifier 28 may be utilized to detect depolarization wave forms associated with the first pacing stimulus (see Block 70). The second sense amplifier 30 is utilized to detect depolarization waveforms associated with the second pacing stimulus (see Block 70). Alternatively, the physician may utilize an external depolarization monitor 88 to detect depolarization waveforms associated with the first and second pacing stimulus. Those skilled in the art will appreciate that a single sense amplifier in conjunction with a switching means of known suitable construction may be utilized instead of two independent sense amplifiers.

A determination is then made whether the first pacing stimulus evokes a response in the heart (see Decision Block 72). If the first pacing stimulus does not evoke a response, a determination is then made whether the second pacing stimulus evokes a response (see Decision Block 74). If the second pacing stimulus does not evoke a response, the auto-capture verification mode is terminated and normal pacing resumes (see Loop 76 and Block 78). If the first pacing stimulus does not evoke a response but the second pacing stimulus evokes a response, then the first stimulus pacing output is reset to the preset value and the second pacing stimulus output is reduced (see Loop 80 and Block 82) and capture verification continues (see Block 66). If the first pacing stimulus evokes a response, a determination is then made whether the second stimulus evokes a response (see Decision Block 84). If the second pacing stimulus does not evoke a response, the second pacing stimulus is returned to the pretest value and the first pacing stimulus output is reduced (see Block 92) and capture verification continues (see Block 66). If, however, both the first and second pacing stimulus evoke a response, the pacing output for the first and second stimulus is then reduced (see Block 82) and capture verification continues (see Loop 96 and Block 66).

In conjunction with reference to FIG. 4, the method of remote activation and monitoring will be discussed in greater detail. The rhythm management device 10 is implanted in the patient and leads 20 and 22 extend into the patient's heart 12. When a magnet 86 having a magnetic field of predetermined strength is brought into proximity of the cardiac rhythm management device 10, an algorithm for cardiac capture verification programmed within the device is initiated. While the device 10 is in the capture verification mode, a physician can monitor the patient's depolarization response via the external depolarization monitor 88. The physician may determine whether the pacing pulses delivered by the cardiac rhythm management device 10 causes capture in the patient's heart, by knowing the capture verification protocol implemented by the cardiac rhythm management device 10.

During the capture verification mode a series of uni-ventricular stimulations may be delivered prior to transmitting stimulation to the other ventricle. In one embodiment of the present invention, the device is cycled through a uni-ventricular pacing mode quickly to limit the loss of pacing support and resulting discomfort and risk to the pacemaker dependent patient. Alternatively, a sequence of fewer than three uni-ventricular pacing pulses could be delivered to each chamber. For example, two stimulations to the left ventricle could be delivered followed by two stimulations to the right ventricle, and then normal pacing may resume.

In order to improve pacing support during the capture verification mode a bi-ventricular pacing sequence could be implemented between the periods of uni-ventricular pacing (stimulating the left and right ventricles individually). During the capture verification mode, if bi-ventricular pacing precedes the uni-ventricular pacing pulses, the resulting signals may also be utilized to confirm that the device is operating under the capture verification mode. A further modification to the capture verification mode of the present invention may include delivering stimulation to the left and right ventricles during the capture verification mode having reduced energy output on subsequent paces. For example, bi-ventricular pacing may be followed by a first left ventricular pacing stimulus having a first energy output and a second reduced left ventricular pacing stimulus followed by a bi-ventricular pacing sequence having varied pacing output followed by a first right ventricular pacing stimulus and a second reduced right ventricular stimulus output. Those skilled in the art will appreciate that each of the above described stimulation modes may be useful depending upon the particular condition of the patient and desired capture verification mode.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device for treating congestive heart failure in a patient wherein the device is adapted to determine whether a stimulation pulse applied to more than one location in the heart evokes a corresponding response for each location, said devices comprising:

(a) stimulation means for sequentially transmitting at least first and second stimulation pulses to different areas of the heart;

(b) detection means for independently detecting an evoked response associated with each of the first and second stimulation pulses; and (c) a controller connected to the stimulation means and detection means, wherein said controller implements a predetermined capture verification mode when said mode is activated.

2. The device as recited in claim 1, wherein said controller is activated by an externally applied magnetic field that activates a switch coupled to said controller.

3. The device as recited in claim 2, wherein said first stimulation is directed to a right ventricle of the patient and the second stimulation is directed to a left ventricle of the patient.

4. The device as recited in claim 1, wherein said first stimulation is directed to a right ventricle of the patient and the second stimulation is directed to a left ventricle of the patient.

5. The device as recited in claim 1, wherein said first stimulation is directed to a ventricle of the patient and the second stimulation is directed to a ventricle of the patient.

6. The device as recited in claim 1, wherein said first stimulation is directed to a right atrium of the patient and the second stimulation is directed to a left atrium of the patient.

7. The device as recited in claim 1, wherein said first stimulation is directed to an atrium of the patient and the second stimulation is directed to an atrium of the patient.

8. The device as recited in claim 1, wherein a predetermined number of first stimulation pulses are transmitted prior to transmitting the second stimulation pulse.

9. The device as recited in claim 1, wherein a predetermined number of third stimulation pulses are transmitted after transmitting the first stimulation pulse but before transmitting the second stimulation pulse.

10. The device as recited in claim 1, wherein a stimulation energy of the first stimulation pulse is varied by a predetermined amount.

11. The device as recited in claim 1, wherein a stimulation energy of the second stimulation pulse is varied by a predetermined amount.

12. A cardiac rhythm management device for treating congestive heart failure in a patient wherein the device may be implemented to determine whether a stimulation evokes a response for each pre-selected chamber, said device comprising:

(a) a pulse generator that sequentially transmits at least first and second stimulation pulses during a cardiac cycle to different areas of the heart;

(b) a detector that independently detects an evoked response associated with each of the first and second stimulation pulses; and (c) a controller connected to the pulse generator and detector, wherein said controller implements a predetermined capture verification mode when said mode is activated.

13. The device as recited in claim 12, wherein said controller is activated by an externally applied magnetic field that activates a switch coupled to said controller.

14. The device as recited in claim 13, wherein said first stimulation is directed to a right ventricle of the patient and the second stimulation is directed to a left ventricle of the patient.

15. The device as recited in claim 12, wherein said first stimulation is directed to a right ventricle of the patient and the second stimulation is directed to a left ventricle of the patient.

16. The device as recited in claim 12, wherein said first stimulation is directed to a ventricle of the patient and the second stimulation is directed to a ventricle of the patient.

17. The device as recited in claim 12, wherein said first stimulation is directed to a right atrium of the patient and the second stimulation is directed to a left atrium of the patient.

18. The device as recited in claim 12, wherein said first stimulation is directed to an atrium of the patient and the second stimulation is directed to an atrium of the patient.

19. The device as recited in claim 12, wherein a predetermined number of first stimulation pulses are transmitted prior to transmitting the second stimulation pulse.

20. The device as recited in claim 12, wherein a predetermined number of third stimulation pulses are transmitted after transmitting the first stimulation pulse but before transmitting the second stimulation pulse.

21. The device as recited in claim 12, wherein a stimulation energy of the first stimulation pulse is varied by a predetermined amount.

22. The device as recited in claim 12, wherein a stimulation energy of the second stimulation pulse is varied by a predetermined amount.

* * * * *